United States Patent
Park (10) Patent No.: US 8,784,105 B2
(45) Date of Patent: Jul. 22, 2014

(54) METHOD OF FABRICATING IMPLANT WITH IMPROVED SURFACE PROPERTIES AND IMPLANT FABRICATED BY THE SAME METHOD

(75) Inventor: Jin Woo Park, Suseong-gu (KR)

(73) Assignee: Osteoph I Co., Ltd., Daegu (KR)

( * ) Notice: Subject to any disclaimer, the term of this patent is extended or adjusted under 35 U.S.C. 154(b) by 791 days.

(21) Appl. No.: 12/452,181

(22) PCT Filed: May 7, 2008

(86) PCT No.: PCT/KR2008/002556
§ 371 (c)(1),
(2), (4) Date: Dec. 16, 2009

(87) PCT Pub. No.: WO2009/011489
PCT Pub. Date: Jan. 22, 2009

(65) Prior Publication Data
US 2010/0136506 A1    Jun. 3, 2010

(30) Foreign Application Priority Data

Jul. 19, 2007    (KR) .................. 10-2007-0072298

(51) Int. Cl.
*A61C 8/00*    (2006.01)
(52) U.S. Cl.
USPC ...................................... 433/201.1
(58) Field of Classification Search
USPC .............. 433/201.1, 172–176; 623/901
See application file for complete search history.

(56) References Cited

U.S. PATENT DOCUMENTS

| | | | |
|---|---|---|---|
| 5,478,237 A * | 12/1995 | Ishizawa | 433/201.1 |
| 5,683,249 A * | 11/1997 | Ibsen et al. | 433/201.1 |
| 5,730,598 A | 3/1998 | Story et al. | |
| 5,944,524 A | 8/1999 | Hill et al. | |
| 6,069,295 A | 5/2000 | Leitao | |
| 6,905,723 B2 | 6/2005 | Li | |
| 2010/0213071 A1* | 8/2010 | Cigada et al. | 205/147 |

FOREIGN PATENT DOCUMENTS

| | | |
|---|---|---|
| CN | 1775305 | 5/2006 |
| CN | 1927410 | 3/2007 |
| JP | 4-371146 | 12/1992 |
| JP | 9-99053 | 4/1997 |
| JP | 11-19205 | 1/1999 |
| JP | 11-99199 | 4/1999 |
| JP | 2007-143772 | 6/2007 |

* cited by examiner

*Primary Examiner* — Sunil K Singh
(74) *Attorney, Agent, or Firm* — Jordan and Hamburg LLP (57) ABSTRACT

A method of fabricating an implant with improved surface properties and an implant fabricated using the same are provided. The method includes immersing a substrate that has titanium or titanium alloy in electrolytic solution including at least one of the group consisting of phosphate or fluoride ion and strontium ion, and forming an oxide film layer with a surface structure having a fine roughness of a micro scale by making at least one of phosphate or fluoride ion and strontium ion react to the titanium or the titanium alloy of the substrate on a surface of the immersed substrate using hydrothermal reaction associated with temperature, pressure and time conditions.

25 Claims, 9 Drawing Sheets

METHOD OF FABRICATING IMPLANT WITH IMPROVED SURFACE PROPERTIES AND IMPLANT FABRICATED BY THE SAME METHOD

TECHNICAL FIELD

The present invention is directed to a method of fabricating an implant and an implant fabricated by the same, and more particularly, to a method of fabricating an implant with improved surface properties and an implant fabricated by the same.

BACKGROUND ART

Implants generally denote substitutes restoring human body tissues that are lost, and refer grafting of artificially-made teeth in dentistry. That is, the implant is used for a semi-permanent dental grafting of an artificial tooth in a jawbone of a man. In case of a general prosthesis or denture, surrounding teeth and bones are damaged with a lapse of time. However, the implant does not damage surrounding tooth tissues and causes no decay in the tooth while having a function and an appearance similar to those of a natural tooth, so that it can be semi-permanently used.

Titanium and titanium alloy chiefly used as an implant material in dentistry and orthopedics areas is not directly interlocked to osseous tissues generally due to a bioinert property. Therefore, a surface treatment such as coating on a surface of a metallic implant with a material having a bioactive property is performed to afford bioactivity to the implant to increase a clinical success rate.

DISCLOSURE

Technical Problem

The present invention provides a method of fabricating an implant with improved surface properties having an excellent interlocking with osseous tissues and accelerating forming of the osseous tissues.

The present invention also provides an implant with improved surface properties fabricated using the above method.

Advantageous Effects

An implant fabricated according to the present invention has surface properties having a fine roughness in a micro unit that is essential to micromechanical interlocking with osseous tissues within a living body, and includes an oxide film layer bonded with ions that accelerate forming of the osseous tissues. Thus, excellent biocompatibility and significant osseous tissues reaction are accomplished to result in bone fusion improved over that of a conventional implant, and relatively excellent mechanical physical characteristics are provided.

BEST MODE

According to an embodiment of the present invention, there is provided a method of fabricating an implant with improved surface properties, which includes immersing a substrate including titanium or titanium alloy in electrolytic solution including at least one of the group consisting of phosphate or fluoride ion and strontium ion; and forming an oxide film layer with a surface structure having a fine roughness in a micro unit by making at least one of phosphate or fluoride ion and strontium ion react to the titanium or the titanium alloy of the substrate on a surface of the immersed substrate using hydrothermal reaction associated with temperature, pressure and time conditions.

The electrolytic solution including the phosphate ion is prepared using phosphoric acid solution having a concentration of 0.1 wt/% or higher. Also, the electrolytic solution including the fluoride ion is prepared using hydrogen fluoride solution having a concentration of 0.01 wt % or higher. The electrolytic solution including the strontium ionl is prepared using strontium aqueous solution having a concentration of 0.00 μmol/l or higher.

Furthermore, the electrolytic solution may include mineralizer. The mineralizer includes at least one of sodium hydroxide and potassium hydroxide, and the concentration of the mineralizer is 0.1~1 mol/l.

The electrolytic solution may further include at least one of calcium ion and magnesium ion. Also, the electrolytic solution including the calcium ion and the magnesium ion is prepared using calcium solution and magnesium solution each having concentration of 0.001 mol/l or higher, for example.

Also, the hydrothermal reaction is performed under a pressure of 1~20 atm at a temperature of 100~250° C. for an hour or more.

Moreover, the method may further include performing thermal treatment after forming the oxide film layer, and the thermal treatment is performed at a temperature of 300~500° C. for an hour or more.

Pretreatment of performing at least one of sandblasting, etching, cleaning, drying and preserving may be performed after conducting polishing the substrate before the immersing.

Furthermore, washing and drying may be carried out after performing the forming of the oxide film layer.

At this time, a surface roughness (Ra) value of the oxide film layer is 1~5 μm.

According to another embodiment of the present invitation, there is provided an implant with improved surface properties including a substrate including titanium or a titanium alloy. Also provided as a part of the implant is an oxide film layer with a surface structure having a fine roughness of a micro scale, and including at least one of the group consisting of titanium phosphate, strontium titanium and strontium titanium phosphate on a surface of the substrate.

Furthermore, the oxide film layer includes at least one of calcium ion and magnesium ion.

Also, a surface roughness (Ra) value of the oxide film layer may be 1~5 μm.

According to another embodiment of the present invitation, there is provided an implant with improved surface properties including a substrate including titanium or a titanium alloy, and an oxide film layer with a surface structure having a roughness of a micro scale and including at least one of titanium fluoride, strontium titanium and strontium titanium fluoride oxide on a surface of the substrate.

The oxide film layer further includes at least one of calcium ion and magnesium ion.

Also, a surface roughness (Ra) value of the oxide film layer may be 1~5 μm.

MODE FOR INVENTION

Embodiments of the present invention are described in detail in the detailed description and the accompanying drawings. The advantages and features of the present invention and a method of realizing the present invention will be clarified with reference to embodiments which will now be described more fully with reference to the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art. The present invention is defined by definitions recited in the claims only.

Figure 1:
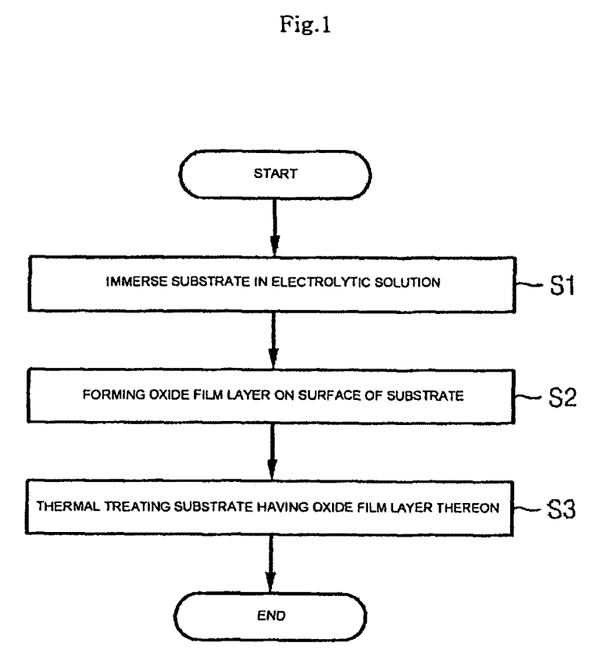
FIG. 1 is a flow chart showing a method of fabricating an implant according to embodiments of the present invention.

A method of fabricating an implant with improved surface properties according to an embodiment of the present invention will be described with reference to FIG. 1. FIG. 1 is a flow chart showing the method of fabricating the implant according to embodiments of the present invention.

Referring to FIG. 1, a substrate is immersed in electrolytic solution including at least one of phosphate ion and strontium ion (S1).

The substrate used in the present invention may include pure titanium, or titanium alloy obtained by titanium added with another metal, i.e., at least one metal selected from the group consisting of aluminum (Al), tantalum (Ta), niobium (Nb), Vanadium (V), zirconium (Zr), tin (Sn), molybdenum (Mo).

More specifically, the substrate may be formed of the pure titanium or one material selected from the group consisting of Ti-6Al-4V, Ti-6Al-7Nb, Ti-30Nb, Ti-13Nb-13zr, Ti-15Mo, Ti-35.3Nb-5.1Ta-7.1Zr, Ti-29Nb-13Ta-4.6Zr, Ti-29Nb-13Ta-25n, Ti-29Nb-13Ta-4.6Sn, Ti-29Nb-13Ta-6Sn, or Ti-16Nb-13Ta-4Mo.

The substrate formed of titanium or titanium alloy may be selectively subjected to pretreatment. For example, a surface of the substrate may be subjected to cutting, etching or sandblasting after the cutting, and cleaning and drying after cutting, etching or sandblasting.

The foregoing substrate is immersed in electrolytic solution. The electrolytic solution is a supply source of supplying at least one of phosphate ion and strontium ion. At this time, the phosphate ion acts for accelerating formation of apatite known as being closely related to ossification, and the strontium ion accelerates proliferation and differentiation of osteoblasts.

Such phosphate ion may be supplied from phosphoric acid ($H_3PO_4$) solution, and the strontium ion may be supplied from solution of strontium oxide (SrO), strontium hydroxide $Sr(OH)_2$, strontium chloride ($SrCl_2$) or strontium chloride hexahydrate ($SrCl_2 6H_2O$), for example. Various kinds of supply sources may be used without being specially restricted to the above described phosphate ion supply source and the strontium ion supply source if they can supply phosphate ion and strontium ion.

At this time, a concentration of the phosphate ion supply source, i.e., the phosphoric acid solution, used in the electrolytic solution may be roughly 0.1 wt % or higher, and preferably roughly 1~5 wt/%, for example. Within the foregoing range of the concentration of the phosphoric acid solution used in the electrolytic solution, excessive decay of the surface of the substrate is prevented and an oxide film layer to an appropriate thickness is formed on the surface of the substrate, which will be described later.

Also, a concentration of the strontium ion supply source, i.e., the strontium aqueous solution, used in the electrolytic solution may be roughly 0.001 mol/l, and preferably roughly 0.001~0.05 mol/l, for example. Using the electrolytic solution, a titanium oxide film layer bonded with strontium can be formed.

The electrolytic solution may further include mineralizer bearing a strong alkaline property. The mineralizer may include at least one of sodium hydroxide (NaOH) and potassium hydroxide (KOH), for example. The mineralizer may have a density of, e.g., about 0.1~1 mol/l in the electrolytic solution, and, within the above-mentioned density range, may form an oxide film layer with a high degree of crystallinity on the surface of the substrate.

Moreover, the electrolytic solution may further include at least one of calcium and magnesium ions. The calcium and magnesium ions act for accelerating attachment of osteoblasts on the surface of the implant to be favorable for the ossification.

For example, the calcium ion may be supplied from calcium oxide (CaO), calcium hydroxide ($Ca(OH)_2$), calcium chloride ($CaCl_2$) solution. The magnesium ion may be supplied from magnesium oxide (MgO), magnesium hydroxide ($MgOH_2$) and magnesium chloride ($MgCl_2$) solution. Various kinds of supply sources may be used without being specially restricted to the above described calcium ion supply source and the magnesium ion supply source if they can supply the calcium ion and the magnesium ion.

At this time, a concentration of the calcium ion supply source or the magnesium ion supply source, i.e., the calcium solution or the magnesium solution, used in the electrolytic solution may be about 0.001 mol/l or higher, and preferably 0.001~0.05 mol/l.

Thereafter, an oxide film layer with a fine roughness of a micro scale is formed on the surface of the substrate using hydrothermal reaction (S2) as shown in FIG. 1.

The substrate immersed in the electrolytic solution may have an oxide film layer with a fine roughness of a micro scale, e.g., 1~5 μm of a surface roughness (Ra) value, on the surface thereof. At this time, since the electrolytic solution includes at least one of the phosphate ion and the strontium ion, the oxide film layer formed on the surface of the substrate may include at least one of phosphate titanium, titanium strontium and strontium titanium phosphate. Moreover, when at least one of the calcium ion and the magnesium ion is included in the electrolytic solution, the oxide film layer may further include at least one of the calcium ion and the magnesium ion.

In order to form the above-described oxide film layer on the surface of the substrate, it is required to perform the hydrothermal reaction under a predetermined pressure at a predetermined temperature for a predetermined time. The hydrothermal reaction may be conducted within a tightly closed hydrothermal reactor coated with Teflon, and performed under a pressure of 1~20 atm at a temperature of about 100~250° C. for about an hour or longer, and preferably 1~24 hours, for example.

In connection with the hydrothermal reaction conditions, the hydrothermal reaction is performed within the above-stated range of the temperature and pressure to facilitate the decay of the surface of the substrate formed of the titanium or the titanium alloy having an excellent corrosion resistance property. Also, the titanium decayed at the surface of the substrate is bonded with ions in the electrolytic solution, i.e., the phosphate ion, the strontium ion, the calcium ion, the magnesium ion, etc., to form the oxide film layer on the surface of the substrate to a thickness of several micrometers.

The substrate having the oxide film layer thereon may be ultrasonic wave washed for several seconds to several tens of minutes using deionized water, and then dried, for example.

Also referring to FIG. 1, thermal treatment may be carried out onto the substrate having the oxide film layer (S3).

A reason of performing the heat treatment on the substrate having the oxide film layer thereon is for preventing degradation of mechanical physical properties caused by hydrogen embrittlement generated during the hydrothermal reaction using an acid. The thermal treatment of the substrate having the oxide film layer thereon may be performed at a temperature of, e.g., about 300~500° C. for an hour, and preferably 1~24 hours.

Then, an implant with improved surface properties is completed using a typical method of fabricating the implant.

Hereinafter, a method of fabricating an implant according to another embodiment of the present invention will be described with reference to FIG. 1. At this time, this embodiment substantially equals to the method of fabricating the implant of the above-described embodiment except that electrolytic solution includes fluoride ion in place of the phosphate ion to make an oxide film layer formed on a surface of a substrate may include titanium fluoride or strontium titanium fluoride oxide. Therefore, this embodiment will be described concentrating on a difference from the above-described embodiment.

As shown in FIG. 1, a substrate is immersed in electrolytic solution including at least one of fluoride ion and strontium ion (S1).

The substrate may be formed including pure titanium or titanium alloy as the above method of fabricating the implant according to the above-described embodiment. The substrate may be selectively subjected to pretreatment. For example, a surface of the substrate may be subjected to cutting, additionally etching or sandblasting after the cutting, and cleaning and drying after cutting, etching or sandblasting.

The resultant substrate is immersed in the electrolytic solution including at least one of the fluoride ion and the strontium ion. At this time, the fluoride ion acts for increasing osseous tissues and accelerating differentiation of the osteoblast closely related to ossification, and the strontium ion accelerates proliferation and differentiation of the osteoblasts.

The fluoride ion may be supplied from hydrofluoric acid (HF) solution, and the strontium ion may be supplied from solution of strontium oxide (SrO), strontium hydroxide $Sr(OH)_2$, strontium chloride ($SrCl_2$) or strontium chloride hexahydrate ($SrCl_2 6H_2O$), for example. Various kinds of supply sources may be used without being specially restricted to the above described fluoride ion supply source and the strontium ion supply source if they can supply the fluoride ion and the strontium ion.

At this time, a concentration of the hydrofluoric acid solution used in the electrolytic solution may be roughly 0.01 wt % or higher, and preferably roughly 0.01~1 wt/%, for example. Within the foregoing range of the density of the hydrofluoric acid solution used in the electrolytic solution, excessive decay of the surface of the substrate is prevented and an oxide film layer to an appropriate thickness is formed on the surface of the substrate, which will be described later.

Also, a concentration of the strontium ion supply source, i.e., the strontium aqueous solution, used in the electrolytic solution may be roughly 0.001 mol/ or higher, and preferably roughly 0.001~0.05 mol/, for example. Using the electrolytic solution, a surface layer where the fluoride ion or the strontium ion is bonded to a titanium oxide film layer can be formed.

The electrolytic solution may further include mineralizer bearing a strong alkaline property, and at least one of the calcium ion and the magnesium ion. A kind and a concentration of the mineralizer, and supply sources and concentrations of the calcium ion and the magnesium ion are substantially identical to those of the above method of fabricating the implant according to the above-described embodiment, which thus will not be described herein. Thereafter, an oxide film layer with a fine roughness of a micro scale is formed on the surface of the substrate using hydrothermal reaction (S2) as shown in FIG. 1.

The substrate immersed in the electrolytic solution may have the oxide film layer with a fine roughness of a micro scale of, e.g., 1~5 of a surface roughness (Ra) value, on the surface thereof. At this time, since the electrolytic solution includes at least one of the fluoride ion and strontium ion, the oxide film layer formed on the surface of the substrate may include at least one of titanium fluoride, titanium strontium and strontium titanium fluoride oxide. Moreover, when at least one of the calcium ion and the magnesium ion is included in the electrolytic solution, the oxide film layer may further include at least one of the calcium ion and the magnesium ion.

In order to form the above-described oxide film layer on the surface of the substrate, it is required to perform the hydrothermal reaction under a predetermined pressure at a predetermined temperature for a predetermined time. The hydrothermal reaction may be conducted within a tightly closed hydrothermal reactor coated with Teflon, and performed under a pressure of 1~20 atm at a temperature of about 100~250° C. for about an hour or longer, and preferably 1~24 hours, for example. In connection with the hydrothermal reaction conditions, the hydrothermal reaction is performed within the above-stated range of the temperature and pressure to facilitate the decay of the surface of the substrate formed of the titanium or the titanium alloy having an excellent corrosion resistance property. Also, the titanium decayed at the surface of the substrate is bonded with ions in the electrolytic solution, i.e., the fluoride ion, the strontium ion, the calcium ion, the magnesium ion, etc., to form the oxide film layer on the surface of the substrate to a thickness of several micrometers.

The substrate having the oxide film layer thereon may be ultrasonic wave washed for several seconds to several tens of minutes using deionized water, and then dried, for example.

Also referring to FIG. 1, thermal treatment may be carried out onto the substrate having the oxide film layer thereon (S3).

A reason of performing the heat treatment on the substrate having the oxide film layer thereon is for preventing degradation of mechanical physical properties caused by hydrogen embrittlement generated during the hydrothermal reaction using acid. The thermal treatment of the substrate having the oxide film layer thereon may be performed at a temperature of, e.g., about 300~500° C. for an hour, and preferably 1~24 hours.

Then, an implant with improved surface properties is completed using a typical method of fabricating the implant.

Now, the present invention will be described in more detail using experimental examples and comparative examples. However, the following experimental examples are provided just for illustrating the present invention without being defined by the following experimental examples.

Experimental Example 1

A substrate was prepared by cutting a commonly used pure titanium plate to a thickness of 1 mm in a dimension of 10×10 mm. A surface of the substrate was ground step by step using a sheet of SiC sand paper of #1200, which was then ultrasonic wave washed sequentially in acetone, alcohol and distilled water solution for 15 minutes each. After washing, the substrate was kept after being air dried within an asepsis worktable.

Thereafter, in order to prepare electrolytic solution including phosphate ion, 2 ml, of orthophosphoric acid solution ($H_3PO_4$) of Sigma Co., ltd. was added to 98 ml of distilled water.

Successively, the electrolytic solution was poured in a Teflon-coated hydrothermal reactor, and the substrate was immersed into the electrolytic solution. Then, the hydrothermal reaction was performed under a pressure of 10 atm at a temperature of 180° C. for 4 hours.

Then, the substrate was ultrasonic wave washed using the distilled water for 20 minutes, and air dried for 24 hours. After this, thermal treatment was performed in an electric furnace at a temperature of about 400° C. for about 12 hours, thereby completing the implant.

Experimental Example 2

A substrate subjected to the pretreatment as the Experimental Example 1 was prepared.

In order to prepare electrolytic solution including phosphate ion and strontium ion, 60 of 85% orthophosphoric acid solution of Sigma Co., ltd., 1.8 g of sodium hydroxide, and 0.6 g of strontium chloride were added to 294 ml of distilled water.

Successively, the electrolytic solution was poured in a Teflon-coated hydrothermal reactor, and the substrate was immersed into the electrolytic solution. Then, the hydrothermal reaction was performed under a pressure of 10 atm at a temperature of 180° C. for 2 hours.

Then, the substrate was ultrasonic wave washed using the distilled water for 20 minutes, and air dried for 24 hours. After this, thermal treatment was performed in an electric furnace at a temperature of about 400° C. for about 12 hours, thereby completing the implant.

Comparative Example 1

A substrate was prepared by cutting a commonly used pure titanium plate to a thickness of 1 mm in a dimension of 10×10 mm. A surface of the substrate was ground step by step using a sheet of SiC sand paper of #1200, which was then ultrasonic wave washed sequentially in acetone, alcohol and distilled water solution for 15 minutes each. After washing, the substrate was kept after being air dried within an asepsis worktable.

Thereafter, in order to prepare electrolytic solution including phosphate, 5 ml of 85% orthophosphoric acid solution of Sigma Co., ltd. was added to 950 of distilled water.

Successively, the electrolytic solution was poured in a Teflon-coated hydrothermal reactor, and the substrate was immersed into the electrolytic solution. Then, the hydrothermal reaction was performed under a normal pressure at a temperature of 80° C. for 24 hours.

Then, the substrate was ultrasonic wave washed using the distilled water for 5 minutes, and air dried for 24 hours. A portion of the substrate was additionally subjected to thermal treatment in an electric furnace at a temperature of about 400° C. for about 12 hours, thereby completing the implant.

Comparative Example 2

After immersing the substrate subjected to the pretreatment as the Comparative Example 1 into 50 mM of strontium aqueous solution, a hydrothermal reaction was performed under a normal pressure at a temperature of 80° C. for 24 hours to complete an implant. Here, a portion of the substrate was additionally subjected to thermal treatment is performed in an electric furnace at a temperature of 400° C. for 12 hours, thereby completing the implant.

Morphological Microstructure of the Surface of the Implant Specimen

Figure 2:
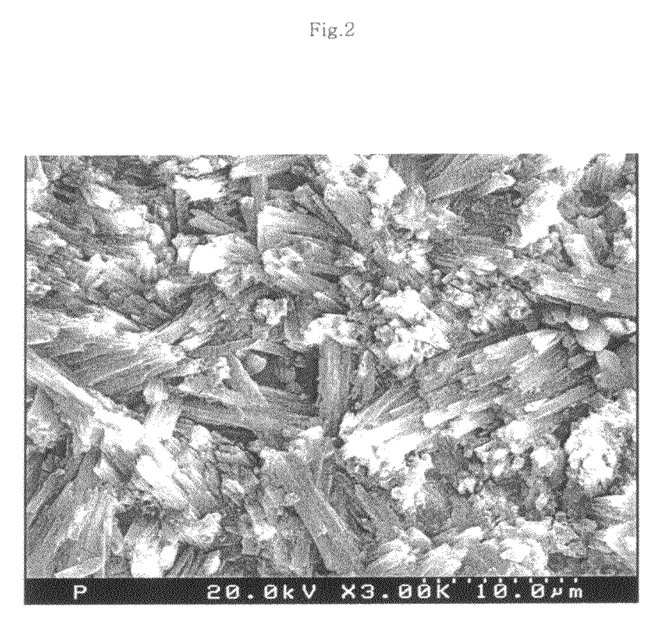
FIGS. 2 and 3 are Scanning Electron Microscopy (SEM) photographs with respect to specimens of Experimental Examples of the present invention.
Figure 3:
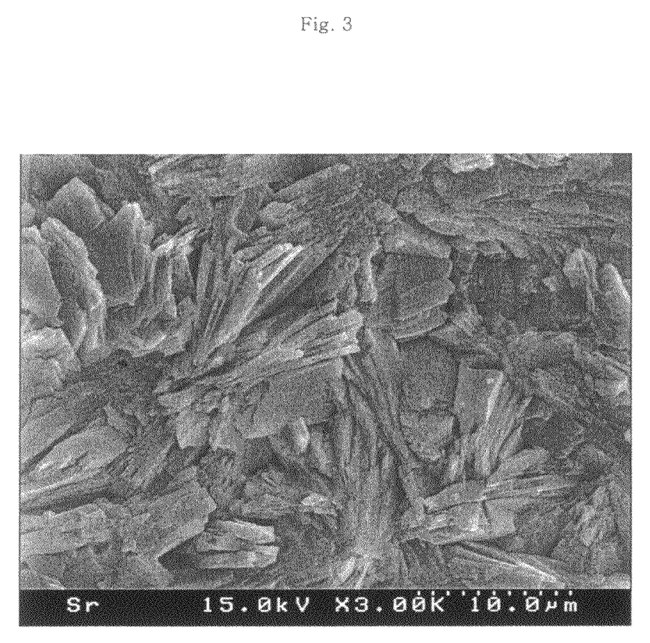
Figure 4:
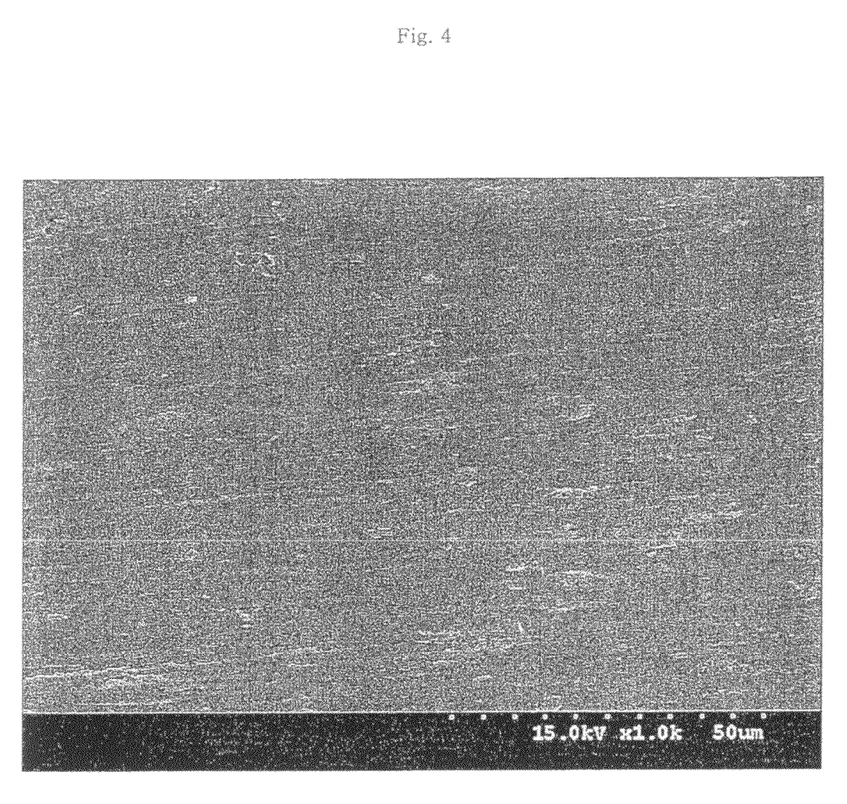
FIG. 4 is an SEM photograph with respect to a specimen of a Comparative Example of the present invention.

Morphological microstructures of the surfaces of Experimental Examples 1 and 2 and Comparative Example 1 are observed by a Scanning Electron Microscopy (SEM), and the results are shown in FIGS. 2 through 4.

FIG. 2 is an SEM photograph with respect to the specimen of Experimental Example 1, and FIG. 3 is an SEM photograph with respect to the specimen of Experimental Example 2. It can be noted that surface structure in a micro unit and a resulting surface roughness in a micro unit are formed on the surfaces of the specimens of Experimental Examples 1 and 2.

FIG. 4 is an SEM photograph with respect to the specimen of the Comparative Example 1. Regardless of performing the thermal treatment, there is no difference on the surface structure when compared with that before conducting the hydrothermal reaction. Furthermore, although not illustrated, the specimen of Comparative Example 2 also has no difference when compared with that before conducting the hydrothermal reaction.

Therefore, it can be confirmed that the fine roughness in the micro unit is formed on the surface of the implants of Experimental Examples 1 and 2 fabricated according to embodiments of the present invention.

Figure 5:
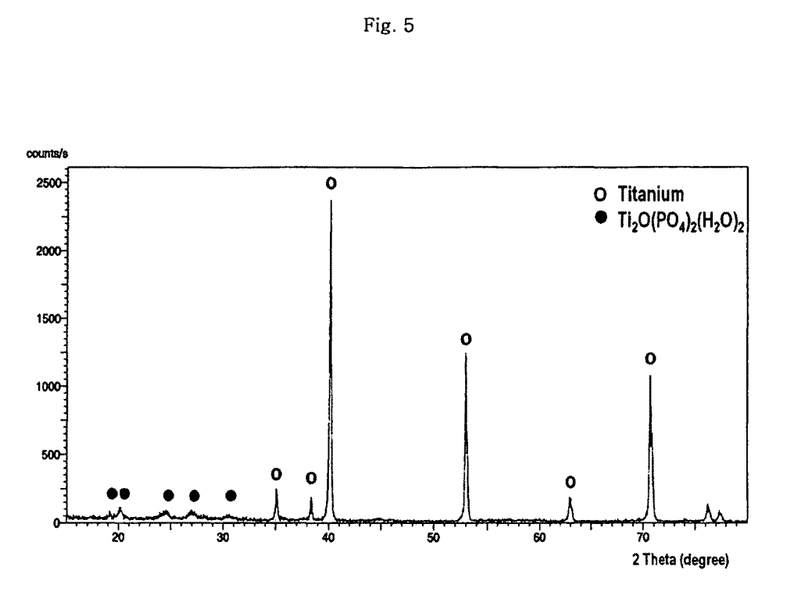
FIGS. 5 through 7 are graphs depicting results of analyzing diffraction of X-rays with respect to the specimens of the Experimental Examples and the Comparative Example.
Figure 6:
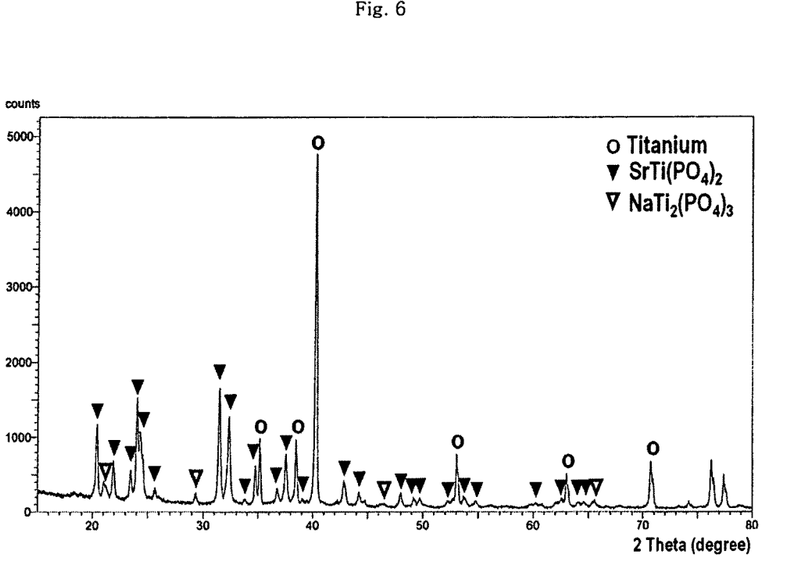
Figure 7:
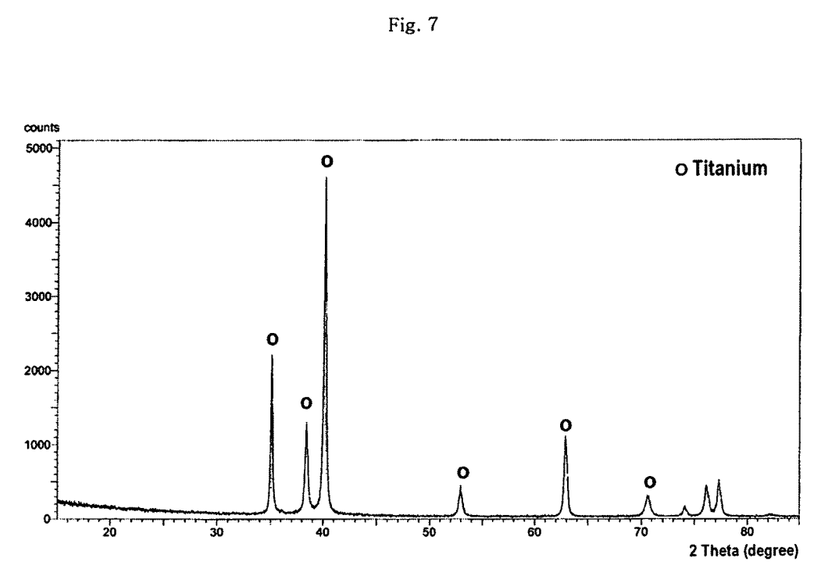

Results of analyzing an X-ray diffraction of the implant specimens of Experimental Examples 1 and 2 and Comparative example 1 are depicted in FIGS. 5 through 7. FIG. 5 is a result of analyzing the X-ray diffraction with respect to the specimen of Experimental Example 1, and FIG. 6 is a result of analyzing the X-ray diffraction with respect to the specimen of Experimental Example of 2. FIG. 7 is a result of analyzing the X-ray diffraction with respect to the specimen of Comparative Example 1. A crystalline structure existing on the surface of the implant is analyzed using a thin-film X-ray diffractometer.

FIG. 5 depicts the analysis result with respect to the specimen of Experimental Example 1, where a peak (JCPDS #88-0563) of titanium phosphate hydrate ($Ti_2O(PO_4)_2(H_2O)_2$) was observed. Also, there was no peak of the titanium hydride different from the specimen that was obtained before performing the thermal treatment and displayed a strong peak of the titanium hydride.

FIG. 6 depicts the analysis result with respect to the specimen of Experimental Example 2, where a peak (JCPDS #33-1356) of strontium titanium phosphate $SrTi(PO_4)_2$ was observed.

FIG. 7 depicts the analysis result with respect to the specimen of Comparative Example 1, where there was no secondary peak of the titanium phosphate besides the titanium peak. Although not illustrated, there was no secondary peak of strontium titanium besides titanium.

In conclusion, it was confirmed that the titanium phosphate or strontium titanium phosphate layer was formed on the oxide film layer on the surface of the implants of the Experimental Examples 1 and 2 fabricated according to the embodiments of the present invention.

Analysis Result of Electron Probe Micro Analyzer Upon Implant Specimens

When the implant specimens of Experimental Examples 1 and 2 and Comparative Examples 1 and 2 were analyzed using X-ray photoelectron spectroscopy, quantitative elemental composition ratios showing the formation of a titanium phosphate hydrate $(Ti_2O(PO_4)_2(H_2O)_2)$ layer in the specimen of Experimental Example 1 and a strontium titanium phosphate $SrTi(PO_4)_2$ layer in the specimen of Experimental Example 2 was confirmed. This result was congruous with the analysis of the X-ray diffraction of the specimens. Meanwhile, the existence of the phosphate ion or the strontium ion could not be confirmed in the specimens of Comparative Examples 1 and 2.

Figure 8:
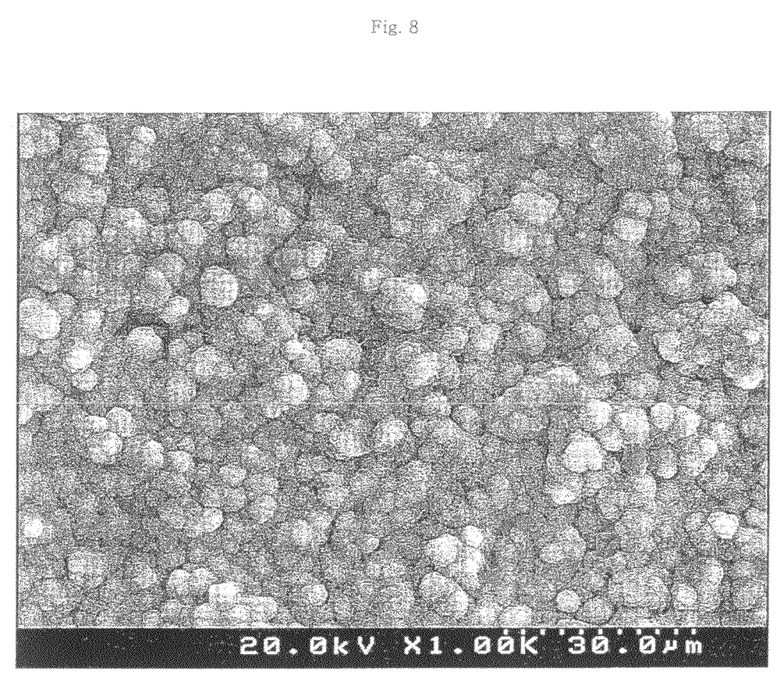
FIGS. 8 and 9 are SEM photographs with respect to surfaces of the specimens after immersing the specimens fabricated by the Experimental Examples in simulated body fluids (Hank's solution) for 4 weeks.
Figure 9:
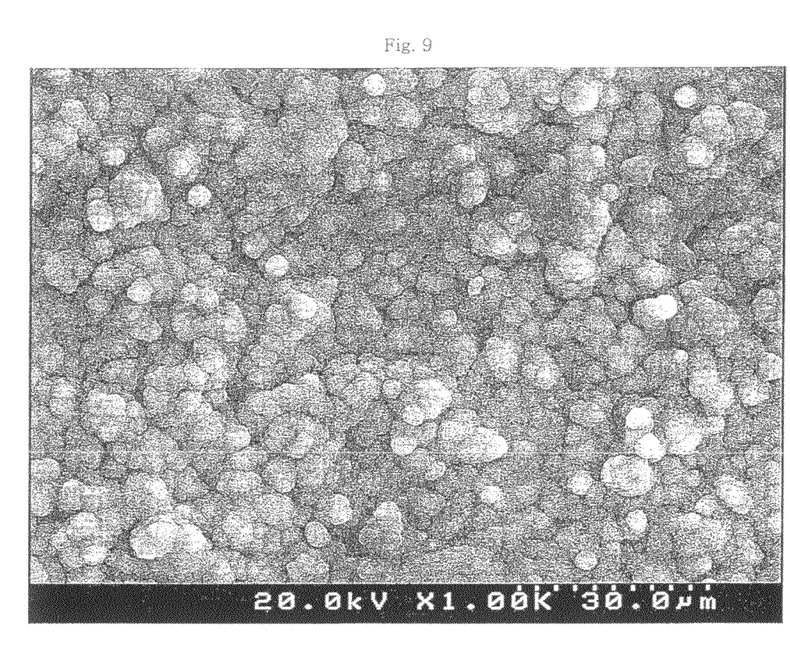

Evaluation of Apatite formation on the Surface of the Implant Specimen in Simulated Body Fluids In order to evaluate bioactivity of the specimens of Experiment Examples 1 and 2, the SEM photographs of the apatite formed on the surfaces are shown in FIGS. 8 and 9 after the specimens are immersed in simulated body fluids (Hank's solution) for 4 weeks.

After elapsing 4 weeks, relatively thick apatite were formed on the overall surfaces of the specimens of Experimental Example 1 (FIG. 8) and Experimental Example 2 (FIG. 9). Although not illustrated, the formation of the apatite was not observed in the specimens of Comparative Examples 1 and 2.

Therefore, it was confirmed that the fabricated specimens had the bioactivity that can accelerate the forming of the osseous tissues. Therefore, the implants of Experimental Examples 1 and 2 fabricated according to the embodiments of the present invention have excellent bio-compatibility. While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

According to the present invention, an implant has a surface structure with a fine roughness in a micro unit essential to micromechanical interlocking with osseous tissues in a living body, and includes an oxide film layer bonded with ions that accelerate the forming of the osseous tissues. Thus, excellent biocompatibility and significant osseous tissues reaction are accomplished to result in bone fusion improved over that of a conventional implant, and relatively excellent mechanical physical characteristics are provided.

The invention claimed is:

1. A method of fabricating an implant with improved surface properties comprising:

pretreating a substrate to expose an uncovered outer surface having titanium or titanium alloy;

immersing the substrate in an electrolytic solution comprising strontium ions to expose the titanium or titanium alloy to the strontium ions; and forming an oxide film layer at the outer surface of the substrate to achieve a surface structure having a fine roughness of a micro scale, said forming including reacting the strontium ions with the exposed titanium or the titanium alloy using a hydrothermal reaction associated with temperature, pressure and time conditions.

2. The method of claim 1, wherein the electrolytic solution further comprises phosphoric acid solution having a concentration of 0.1 wt/% or higher.

3. The method of claim 1, wherein the electrolytic solution further comprises fluoride ions prepared using hydrogen fluoride solution having a concentration of 0.01 wt % or higher.

4. The method of claim 1, wherein the electrolytic solution is prepared using strontium aqueous solution having a concentration of 0.001 mol/l or higher.

5. The method of claim 1, wherein the electrolytic solution further comprises mineralizer.

6. The method of claim 5, wherein the mineralizer comprises at least one of sodium hydroxide and potassium hydroxide.

7. The method of claim 5, wherein the concentration of the mineralizer is 0.1~1 mol/l.

8. The method of claim 1, wherein the electrolytic solution further comprises at least one of calcium ion and magnesium ion.

9. The method of claim 8, wherein the electrolytic solution including the calcium ion and the magnesium ion is prepared using calcium solution and magnesium solution each having concentration of 0.001 mol/l or higher.

10. The method of claim 1, wherein the hydrothermal reaction is performed under a pressure of 1~20 atm at a temperature of 100~250° C.

11. The method of claim 10, wherein the hydrothermal reaction is performed for an hour or more.

12. The method of claim 1, further comprising performing thermal treatment after forming the oxide film layer.

13. The method of claim 12, wherein the thermal treatment is performed at a temperature of 300~500° C. for an hour or more.

14. The method of claim 1, further comprising pretreatment of performing at least one of sandblasting, etching, cleaning, drying and preserving after conducting polishing the substrate before the immersing.

15. The method of claim 1, further comprising washing and drying after performing the forming of the oxide film layer.

16. The method of claim 1, wherein a surface roughness (Ra) value of the oxide film layer is 1~5 μm.

17. An implant with improved surface properties produced by the method of claim 1, comprising:

a substrate including titanium or a titanium alloy; and an oxide film layer provided directly on an outer surface of the substrate providing the implant with a surface structure having a fine roughness on a micro scale, and wherein the oxide film layer is configured at least in part with titanium or titanium alloy at the outer surface of the substrate reacted with strontium ions, so as to include at least one of the group consisting of strontium titanium and strontium titanium phosphate on a surface of the substrate.

18. The implant of claim 17, wherein the oxide film layer further comprises at least one of calcium ion and magnesium ion.

19. The implant of the claim 17, wherein a surface roughness (Ra) value of the oxide film layer is 1~5 μm.

20. An implant with improved surface properties produced by the method of claim 1, comprising:
a substrate including titanium or a titanium alloy; and
an oxide film layer with a surface structure having a roughness in a micro unit and including at least one of strontium titanium and strontium titanium fluoride oxide.

21. The implant of claim 20, wherein the oxide film layer further comprises at least one of calcium ion and magnesium ion.

22. The implant of claim 20, wherein a surface roughness (Ra) value of the oxide film layer is 1~5 μm.

23. The method of claim 1, wherein said forming the oxide film layer consists of applying a prescribed pressure and temperature for a prescribed time period while the substrate is immersed in the electrolyte solution to enact said hydrothermal reaction between the exposed titanium or titanium alloy at the outer surface of the substrate and the electrolytic solution.

24. The method of claim 23, wherein the hydrothermal reaction is performed under a pressure of 1~20 atm at a temperature of 100~250° C. for at least one hour.

25. The method of claim 1, wherein said forming the oxide film layer consists of:
applying a pressure of 1~20 atm for at least one hour while the substrate is immersed in the electrolyte solution; and
performing thermal treatment after said applying, wherein the thermal treatment is performed at a temperature of 300~500° C. for at least one hour; and
wherein said hydrothermal reaction consists of said applying and said performing.

* * * * *